United States Patent [19]

Onodera

[11] 4,278,690

[45] Jul. 14, 1981

[54] **METHOD OF PRODUCING NUTRIENT FOOD BY FERMENTING WATER OATS WITH A *BACILLUS SUBTILIS***

[76] Inventor: Bunei Onodera, Harajukuribin 3F, 2-35-13, Jingumae, Shibuya-ku, Tokyo, Japan

[21] Appl. No.: 71,773

[22] Filed: Aug. 31, 1979

[30] Foreign Application Priority Data

Sep. 13, 1978 [JP] Japan .................................. 53-111765

[51] Int. Cl.$^3$ .......................... A23B 7/02; A23L 1/212
[52] U.S. Cl. .......................................... 426/52; 426/18
[58] Field of Search ...................... 426/49, 18, 52, 618, 426/615, 590

[56] References Cited

U.S. PATENT DOCUMENTS

| 3,157,513 | 11/1964 | Allen et al. .............................. 426/18 |
| 3,709,694 | 1/1973 | Killinger et al. ......................... 426/49 |

FOREIGN PATENT DOCUMENTS 2315995  10/1974  Fed. Rep. of Germany ............. 426/49

*Primary Examiner*—Joseph M. Golian
*Assistant Examiner*—Elizabeth J. Curtin
*Attorney, Agent, or Firm*—Browdy and Neimark

[57] ABSTRACT

The present invention is a method of producing a nutrient food by steam boiling leaves and/or stalks of water oats, inoculating a mutant, *Bacillus subtilis* ON-1, to the resulting boiled material and fementing it. It has been known that water oats become a nutrient food, but according to the prior art method in which the water oats are only dried, the product is poor in quality and the effective part which can be utilized is small in quantity. By inoculating a mutant, *Bacillus subtilis* ON-1, to the water oats and thereby fermenting them, it becomes possible to effectively use almost all of the water oats and also to obtain a superior food in quality.

6 Claims, No Drawings

METHOD OF PRODUCING NUTRIENT FOOD BY FERMENTING WATER OATS WITH A BACILLUS SUBTILIS

The present invention relates to a method of producing a nutrient food from water oats by use of a newly separated mutant, *Bacillus subtilis* ON-1. It has been known that the water oat n which is an autogenous plant, has the effect of a medicine, but heretofore only its roots and leaves have been used, and in the prior art, its stalks have not been used and therefore they have been thrown away. However, the separation of the stalks from the leaves and the disposal thereof have been very troublesome and the amount of the stalks which were disposed was as much as that of the leaves, so that it has been a traditional problem for the concerned technical field to effectively treat the stalks of water oats.

The inventors of the present invention have studied the edibility and effective utilization of the stalks of the water oat, and as a result confirmed that there is a nutrient component in a degree that is not less than that contained in the leaves. In order to produce a nutrient drink and food from the stalks, known treating processes such as heating, crumpling and twisting, enzyme treatment, fermentation treatment and so forth were tried. However, none of the above processes were successful.

Therefore, the present inventors turned their attention to the fermentation treatment. In order to attain the desired object, it was found that existing microorganisms could not be used. Accordingly, the direction of the research changed to the point of view that it is necessary to newly separate a certain microorganism which can attain the desired object. As a result of the continued study of the inventors, new bacteria were separated from the soil in a rice field in Miyagi prefecture in Japan, and it was found that this microorganism could easily ferment the stalks of water oat and make them edible, thereby allowing a drink and food article to be produced, which article was refreshing, sweet-smelling and nutritious. This microorganism was such that had a utility which was very industrially useful, with the result that the present invention has been completed.

This newly separated bacteria has such a characteristic that it has a strong fermentation power that enables it to ferment and make edible not only the stalks of water oat but also the leaves thereof, of course.

Therefore, with use of the present bacteria, since both the leaves and stalks of water oat can be utilized, it is unnecessary to separate the leaves and stalks from each other, so that the treatment step can be simplified resulting in permitting a large reduction of cost, and also since it is possible to use, as raw material, the stalks, which have been thrown away in the prior art, there is also a large effectiveness in the aspects of the simplicity of obtaining the raw material, the mass production of the product and the industrialization.

The newly separated microorganism has the following bacteriological properties, and for reasons described below, although it belongs to *Bacillus subtilis*, it is identified as its mutant and thus named as *Bacillus subtilis* ON-1. This microorganism has been deposited as FERM-P No. 4608 in Fermentation Research Institute, Agency of Industrial Science and Technology in Japan.

Its bacteriological properties are as follows.

A. Morphological properties:
(1) GRAM's stain: Positive
(2) Shape: Rod-shaped microbe having $0.7$–$0.8\mu$ in breadth and $2$–$3\mu$ in length.
(3) Endospore: An egg-shaped endospore of $0.6 \times 1.5$–$1.8\mu$ is formed at the center of the fungus.
(4) Motility property: Existence (having peritrichous)

B. Growth conditions in various kinds of media: (Culture at 37° for 24 hours)
(1) Usual agar medium: Very good growth.
  Clear growth is shown. Occasionally, free-running property is recognized.
(2) Yeast extract medium: Thickly raised colony is produced.
(3) Malt extract medium: Thickly raised colony is produced.
(4) Acidic agar medium (Proteose): Flower-shaped thick colony is produced.
(5) Soy bean agar medium: Thick colony is produced.
(6) Saburo agar medium: Very bad growth.
(7) Glucose liquid medium: Film growth is shown.
(8) Table salt liquid medium: 10%: No growth. 5%: Growth is shown.
(9) Neutral red agar medium: Growth is shown.
(10) Potato starch liquid medium: Growth is shown.

Physiological properties:
(1) Optimum growth temperature: 28°–37° C.
(2) Growth in usual agar medium at 65° C.: No growth by culture at 65° C. for 24 hours.
(3) Minimum growth pH: 1.0
(4) pH after 7-day culture in liquid medium: 7.2–7.8
(5) Growth by high pressure treatment after culture in bouillon medium at 37° C. for 24 hours: No growth is shown immediately after the addition of high pressure, and by the culture at 37° C. for 24 hours, growth is shown as before.
(6) Spore after high pressure sterilization treatment: Even after high pressure sterilization at 121° C. for 30 min. of liquid cultured microbe spores of the present microbe are alive.
(7) Utility of sugar:
  (1) Glucose: Decomposition
  (2) Xylose: No decomposition
  (3) Arabinose: No decomposition (Occasionally there are cases where decomposition is shown.)
  (4) Mannitol: No decomposition (In the case of culture for a longer period, decomposition occurs occasionally.)
  (5) Lactose: No decomposition
(8) Liquefaction of gelatin: Liquefaction occurs.
(9) Hydrolysis of starch: Decomposition occurs.
(10) Methylcarbinolacetyl VP reaction: Positive
(11) Production of hydrogen sulfide (Titorato): Production occurs.
(12) Generation of Indole: No generation
(13) Litmus milk: Solidification occurs and reduction of litmus is caused.
(14) Lecithinase: Negative
(15) Reduction of nitrate: Reduction occurs.
(16) Decomposition of urea: No decomposition.
(17) Production of gas: No production Judging from the above properties with reference to Bergey's Manual of Determinative Bacteriology (Eighth edition), viewed from the growth condition on bouillon liquefied medium, the rod-shaped bacteria which form egg-shaped endospore at the center, and its aerobic property, it is apparent that the present strain belongs to the Bacillus genus, and as its similar fungi there are *Bacillus pumilus* and *B. licheniformis.* However, the present strain differs from *Bacillus pumilus* in the points of the breadth of fungus, the hydrolysis of starch and the reduction of nitrate, and it is also distinguished from the other similar strain, *Bacillus licheniformis* in the point of the length of microbe and the temperature of growth. Thus, it is thought after all that it is most proper to determine that the present strain belongs to *Bacillus subtilis.*

However, the present strain differs from *Bacillus subtilis* in the following points. Namely, xylose and arabinose may be occasionally decomposed, but generally do not decompose, and as well mannitol may be decomposed in the case of a longer culture, but generally does not decompose, and its growth on Saburo culture is very bad. More essentially, the present strain has a very useful and superior physiological property in that it breaks the structure of stalks and leaves of water oats thereby contributing to the dissolving-out of effective constituents therein, and more particularly it makes the stalks of water oat edible, and on the contrary *Bacillus subtilis* does not show such properties at all. Accordingly, it is thought to be unreasonable that the present strain belongs to *Bacillus subtilis* as it is, but thought to be reasonable that it is a variant of *Bacillus subtilis,* and therefore it has been named *Bacillus subtilis* ON-1, a new variant of *Bacillus subtilis.*

The present invention relates to the method of producing an eating and drinking article rich in nutrient by making the stalks and leaves of water oat edible by use of this new variant, and the details are as follows.

At first the reaped water oats are dried. This drying treatment is done to make the subsequent treatments of steam boiling and fermentation treatment effective, and therefore done in such a way that according to the efficiency of a steam-boiling apparatus they are dried to an appropriate extent between a semidried condition and a dried condition, but in general it is preferable to make them as dry as possible. Therefore the drying may be carried out in a drying oven or naturally by use of the sun light.

Next, the dried water oats are cut into pieces, and in this case, according to the present invention, it is possible to cut them together with their leaves without separating the stalks therefrom, so that the present invention does not necessitate the troublesome step of the stalk separating operation, thereby resulting in a remarkable simplification of steps and reduction of cost. One of the important features of the present invention is to enable utilization of the stalks as well as the leaves. The stalks of water oat are cut into pieces of appropriate sizes, and usually preferably from 1 mm to 10 cm. The resulting cut stalk pieces may have dirt adhering thereto, and therefore these are washed by water to remove the dirt, but it is necessary to perform this cleaning treatment under a sufficient attention so as not to cause breaking of the constituents of the leaves and stalks, particularly of the leaves. The cleaning treatment can be done before the cutting treatment.

The resulting pieces are steam boiled by use of steam at 100°–150° C. for 30 min. to 5 hours to subject the water oats to a high temperature sterilization thereby preventing them from contamination by infectious microbes and at the same time to cause the composition parts of the leaves and stalks to be expanded and roughed so as to enable the subsequent fermentation treatment easy. After the steam boiling treatment, the resulting material is naturally or forcibly cooled to 10°–50° C., preferably 30°–40° C.

Now, *Bacillus subtilis* ON-1 is inoculated to said material. As microbe to be inoculated, a pure culture of *Bacillus subtilis* ON-1, a mixture of propagated microbe obtained by the culture of said cultured substance and the medium, the water oats themselves applied with the microbe or their spores, etc., can be appropriately used. Also, the spores of the present microbe can be inoculated. However, in this case, it takes a longer time to complete the fermentation. But since these spores have a very high heat-resisting property, there is an advantage that if the spores are inoculated immediately after the steam boiling and thus the fermentation is caused in as aseptic fermentation room, the product can be obtained without any contamination from infectious microbes.

As described above, after the inoculation of the present microbe the material is fermented in a fermentation room. As the fermentation room, there may be widely used various types ranging from a modern one in which temperature and humidity can be adjusted and contamination by infectious microbes can be completely prevented, to a conventional type room (Muro). Upon the fermentation, the temperature is maintained within a range of 15°–55° C., but it is preferable to maintain a temperature of 28°–37° C. which is an optimum growth temperature for the present fungi. The period necessary for the fermentation may vary depending on the quality of the water oats, the condition of the drying the condition of the steam boiling, the condition of the inoculation, the condition of the fermentation etc. However, in general, a period of 5–15 days may be enough. Due to this fermentation treatment, cellulose etc. become decomposed and edible, and the cells are partly broken down thereby permitting the nutriments to be dissolved out and become easy to be absorbed into a human body resulting in effective nutrition.

After the end of the fermentation, the material is completely dried by the sun light or a drier, and ground into fine powder by means of an air-separation type mill or smashed into pieces by means of a shearing machine to produce a product.

The product thus produced is almost tasteless and odorless, and it may be used for drinking in such a way that it is dissolved in water or hot water or decocted as it is or in the form of a tea bag formed as a permeable bag. It is of course possible to use as a mixture for the addition to a usual tea, milk, soda pop, etc. Moreover, this product has a good miscibility to other foods. In addition to the use for drinking, it is also possible to widely use it as an additive to various foods such as chewing gum, bread, cake, noodles, flavored ice on a stick, milk product, paste-like product, soy bean product, various kinds of fermentation foods, etc.

Hereinafter, some embodiments of the present invention will be explained.

PRACTICAL EXAMPLE 1

After the sun light drying of the reaped water oats, they are cut into pieces of 1 cm in length as they are, without the separation of the leaves from the stalks, and the cut pieces are water washed. These pieces are steam boiled by use of steam at 100°–120° C. for 4 hours in a steam cooking pot, and then cooled to 35° C.

The resulting material is inoculated with *Bacillus subtilis* ON-1 (FERM-P No. 4608) which has previously been cultured in the bouillon liquid medium, and in a fermentation room, it is fermented at 35° C. for ten days. The resulting fermented material is dried in a drier and thereafter crushed to obtain a fine powdered product.

PRACTICAL EXAMPLE 2

300 g of the water oat powder obtained by Practical example 1 was dissolved in 2 l of an orange juice having 100 g of sugar dissolved therein. The resulting solution was added with 1 g of sodium polyphosphate, 0.4 g of sodium metaphosphate, 0.4 g of sodium pyrophosphate and 0.2 g of sodium phosphate, and after the mixing and dissolving of the above components, the resulting solution was spray dried to obtain a powdered juice containing water oat.

The powdered juice was dissolved in cold water and the resulting juice was tested by 30 test drinkers, and as a result it was recorded that it has substantially no discomforting smell, discomforting taste or foreign matter feeling to the tongue, which are unsuitable for the drink.

PRACTICAL EXAMPLE 3

500 g of skim milk was put into 500 g of water, and heated while stirring it, and when it reached about 50° C. a solution was added to it, which solution was formed by dissolving 400 g of sugar, 200 g of glucose and 10 g of carboxymethylcellulose in 200 g of water, and the resulting mixture was heated at 60° C., and then this mixture was cooled to 20° C., and a solution formed by dissolving 40 g of the water oat powder obtained by Practical example 1 in 150 g of water and a small amount of a flavor (Vanilla) is added. After homogenizing by means of a homogenizer, it was subjected to a sieving treatment through a 120-mesh sieve, and thereafter sterilized at 120° C. for 15 sec. by means of a plate type sterilizer, and then frozen to produce an ice cream containing water oat powder.

What is claimed is:

1. A method of producing a nutrient food from water oats, comprising:
   drying the water oats;
   cutting the leaves, stalks or both leaves and stalks of water oats into small pieces;
   steam boiling the cut pieces;
   cooling the steam boiled material;
   fermenting the cooled material with *Bacillus subtilis* ON-1; and
   drying the fermented material.
2. A method in accordance with claim 1, wherein said steam boiling step takes place at 100°–150° C.
3. A method in accordance with claims 1 or 2, wherein said fermenting step takes place at 15°–55° C. for 5–15 days.
4. A method in accordance with claim 3 wherein said cooling step comprises cooling the steam boiled material to 10°–15° C.
5. A method in accordance with claim 3, further including the step of crushing the dried fermented material into a fine powder.
6. A method in accordance with claim 1 or claim 2, further including the step of crushing the dried fermented material into a fine powder.

* * * * *